United States Patent
Brousseau, III

(10) Patent No.: US 7,208,784 B2
(45) Date of Patent: *Apr. 24, 2007

(54) SINGLE-ELECTRON TRANSISTOR FOR DETECTING BIOMOLECULES

(75) Inventor: Louis C. Brousseau, III, Austin, TX (US)

(73) Assignee: Quantum Logic Devices, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/015,043

(22) Filed: Dec. 17, 2004

(65) Prior Publication Data

US 2005/0230713 A1   Oct. 20, 2005

Related U.S. Application Data

(63) Continuation-in-part of application No. 10/680,871, filed on Oct. 7, 2003, now abandoned.

(51) Int. Cl.
*H01L 29/76* (2006.01)

(52) U.S. Cl. .................. 257/253; 257/213; 257/69; 257/14; 257/17; 257/20; 257/24; 257/30; 257/39; 257/414; 257/624

(58) Field of Classification Search .............. 257/30, 257/24, 39, 37, 28, 253, 414, 622, 623, 624
See application file for complete search history.

(56) References Cited

U.S. PATENT DOCUMENTS 5,828,076 A * 10/1998 Gossner et al. ............... 257/24
6,653,653 B2 * 11/2003 Brousseau, III .............. 257/39
6,958,216 B2 * 10/2005 Kelley et al. .................. 435/6
2004/0113144 A1 * 6/2004 Brousseau, III .............. 257/39

* cited by examiner

*Primary Examiner*—Evan Pert
*Assistant Examiner*—Fazli Erdem
(74) *Attorney, Agent, or Firm*—Antony P. Ng; Dillon & Yudell LLP

(57) ABSTRACT

A single-electron transistor includes a projecting feature, such as a pyramid, that projects from a face of a substrate. A first electrode is provided on the substrate face that extends onto the projecting feature. A second electrode is provided on the substrate face that extends onto the projecting feature and that is spaced apart from the first electrode. Accordingly, the geometric configuration of the projecting feature can define the spacing between the first and second electrodes. At least one nanoparticle is provided on the projecting feature between the first and second electrodes. The single-electron transistors may be fabricated by forming a projecting feature on a substrate that projects from a face thereof, forming a first electrode on the substrate face that extends onto the projecting feature, forming a second electrode on the substrate face that extends onto the projecting feature and that is spaced apart from the first electrode, and placing at least one nanoparticle on the projecting feature between the first and second electrodes. The single-electron transistor fabricated in this way may be used as a detector for biomolecular reactions by attaching a probe molecule to the surface of the nanoparticle and measuring changes in the electronic signal obtained from the device.

6 Claims, 10 Drawing Sheets

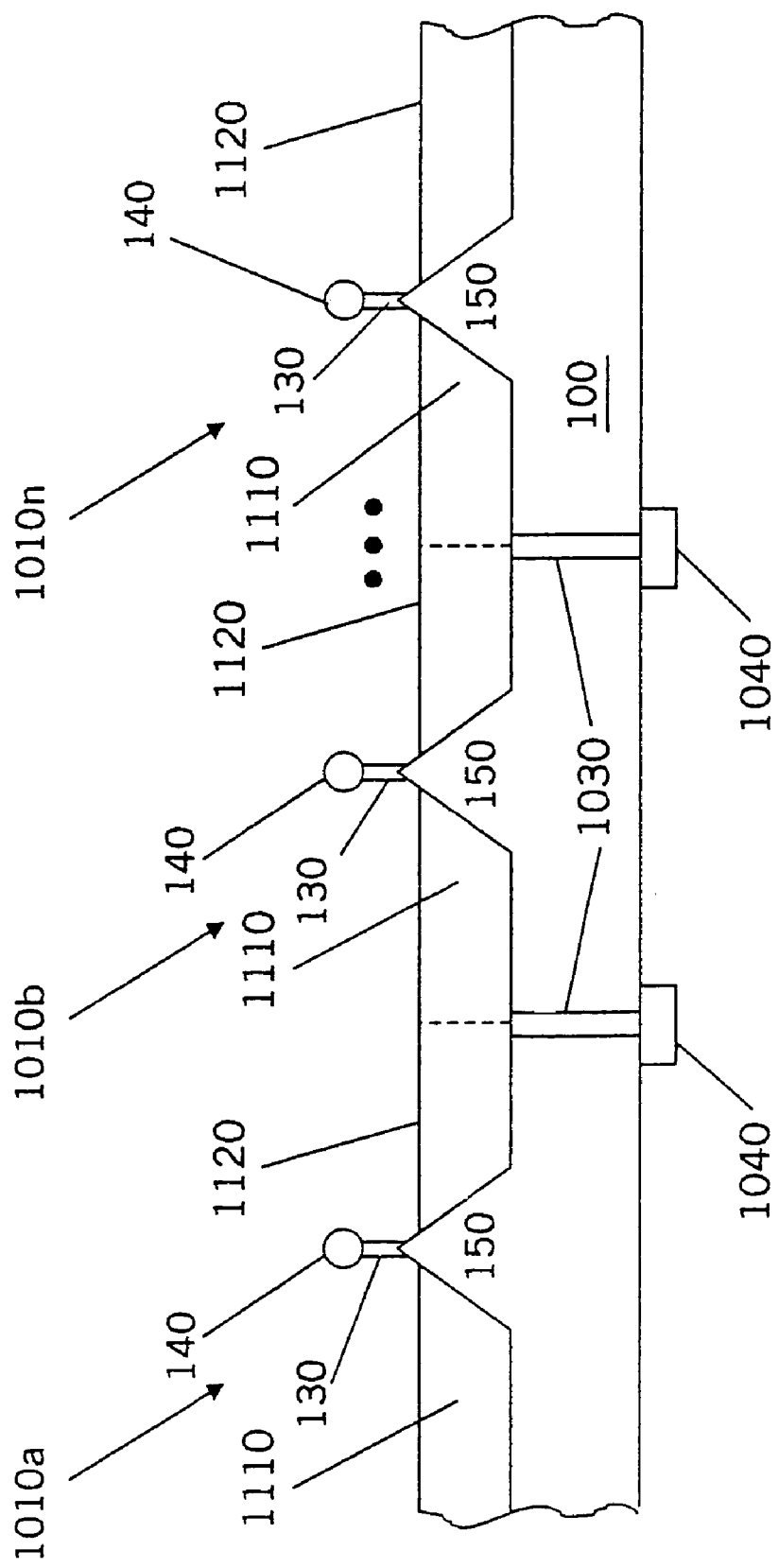

SINGLE-ELECTRON TRANSISTOR FOR DETECTING BIOMOLECULES

RELATED PATENT APPLICATIONS

The present patent application is a continuation in-part related to application U.S. Ser. No. 10/680,871 filed on Oct. 7, 2003, now abandoned.

BACKGROUND OF THE INVENTION

1. Technical Field

The present invention relates to microelectronic devices in general, and in particular to a single-electron transistor for detecting biological molecules.

2. Description of the Related Art

Single-electron Transistor (SET) devices and fabrication methods are being widely investigated for high density and/or high performance microelectronic devices. As is well known to those having skill in the art, single-electron transistors use single-electron nanoelectronics that can operate based on the flow of single-electrons through nanometer-sized particles, also referred to as nanoparticles, nanoclusters or quantum dots. Although a single-electron transistor can be similar in general principle to a conventional Field Effect Transistor (FET), such as a conventional Metal Oxide Semiconductor FET (MOSFET), in a single-electron transistor, transfer of electrons may take place based on the tunneling of single-electrons through the nanoparticles. Single-electron transistors are described, for example, in U.S. Pat. Nos. 5,420,746; 5,646,420; 5,844,834; 6,057,556 and 6,159,620, and in publications by the present inventor Brousseau, III et al., entitled *pH-Gated Single-Electron Tunneling in Chemically Modified Gold Nanoclusters*, Journal of the American Chemical Society, Vol. 120, No. 30, 1998, pp. 7645–7646, and by Feldheim et al., entitled *Self-Assembly of Single Electron Transistors and Related Devices*, Chemical Society Reviews, Vol. 27, 1998, pp. 1–12, and in a publication by Klein et al., entitled *A Single-Electron Transistor Made From a Cadmium Selenide Nanocrystal*, Nature, 1997, pp. 699–701, the disclosures of which are hereby incorporated herein by reference in their entirety as if set forth fully herein.

A major breakthrough in single-electron transistor technology is described in U.S. patent application Ser. No. 09/376,695, entitled *Sensing Devices Using Chemically-Gated Single Electron Transistors*, by Daniel L. Feldheim and Louis C. Brousseau, III, also published as International Publication No. WO 01/13432 A1, the disclosures of which are hereby incorporated herein by reference in their entirety as if set forth fully herein. Described therein is a chemically-gated single-electron transistor that can be adapted for use as a chemical or biological sensor. Embodiments of these chemically-gated single-electron transistors include source and drain electrodes on a substrate and a nanoparticle between the source and drain electrodes, that has a spatial dimension of a magnitude of approximately 12 nm or less. An analyte-specific binding agent is disposed on a surface of the nanoparticle. A binding event occurring between a target analyte and the binding agent causes a detectable change in the characteristics of the single-electron transistor.

Notwithstanding these and other configurations of signle-electron transistors, including chemically-gated single-electron transistors, it may be difficult to fabricate these devices using conventional photolithography that is employed to fabricate microelectronic devices. In particular, in order to provide quantum mechanical effects with nanoparticles, it may be desirable to provide spacing between the source and drain electrodes of a single-electron transistor that is less than about 20 nm, or less than about 12 nm or about 10 nm. It may be difficult, however, to provide these spacings using conventional lithography at low cost and/or with acceptable device yields.

SUMMARY OF THE INVENTION

Embodiments of the present invention provide single-electron transistors and manufacturing methods therefor, in which a projecting feature, such as a pyramid, projects from a face of a substrate. A first electrode is provided on the substrate face that extends onto the projecting feature. A second electrode is provided on the substrate face that extends onto the projecting feature and that is spaced apart from the first electrode. At least one nanoparticle is provided on the projecting feature between the first and second electrodes. Accordingly, the geometric configuration of the projecting feature can define the spacing between the first and second electrodes. A desired spacing between the first and second electrodes therefore may be obtained without the need for high-resolution photolithography.

Embodiments of the present invention may stem from a realization that projecting features, such as pyramids, can be fabricated on a substrate, using conventional microelectronic fabrication techniques. The projecting feature, such as a pyramid, may have a small vertex. Thus, first and second electrodes that are formed on the projecting feature, adjacent the vertex, can have small spacing therebetween, such as less than about 20 nm or less than about 12 nm or about 10 nm, whereas it may be difficult to photolithographically define a region in a layer that is, for example, 10 nm wide. Accordingly, single-electron transistor devices may be fabricated using conventional microelectronic techniques, with the potential of low cost and/or high yields. It will be understood that, as used herein, the term "vertex" applies to a region on a surface of a pyramid where the sides of the pyramid intersect or approach one another. The vertex need not be the highest or lowest point of the pyramid.

Single-electron transistors according to other embodiments of the present invention comprise a substrate including a pyramid that projects from a face thereof. The pyramid includes a plurality of sides and a vertex. A first electrode is provided on a first side of the pyramid, including a first electrode end that extends adjacent the vertex. A second electrode is provided on the second side of the pyramid, and includes a second electrode end that extends adjacent the vertex and that is spaced apart from the first electrode end. At least one nanoparticle is provided on the vertex. In some embodiments, the first electrode end and the second electrode end are spaced apart by less than about 20 nm adjacent the vertex. In other embodiments, the first electrode end and the second electrode end are spaced apart by about 10 nm adjacent the vertex. In some embodiments, the vertex is a point, whereas in other embodiments, the vertex is a plateau (i.e., flat).

In some embodiments, the feature such as a pyramid projects outwardly, away from the face of the substrate, to provide a feature such as a pyramid that rises from the substrate face. In other embodiments, the feature such as a pyramid projects inwardly from the face of the substrate into the substrate, to provide a trench such as a pyramidal-shaped trench that extends into the substrate. In some embodiments, the pyramid includes four sides, and the first and second sides, on which the respective first and second electrodes are provided, are opposite one another.

In some embodiments, the first and second electrodes are free of nanoparticles thereon. In other embodiments, the at least one nanoparticle comprises a plurality of nanoparticles on the vertex, on the first electrode end, and/or on the second electrode end.

In other embodiments of the present invention, multiple single-electron transistors may be provided on a substrate, including a plurality of features such as pyramids, a plurality of first electrodes, and a plurality of second electrodes. At least one nanoparticle may be provided on the vertex of the pyramids. The first and second electrodes of adjacent transistors may be electrically connected together. Stated differently, an electrode may be provided that extends from a side of a pyramid to a side of an adjacent pyramid.

In yet other embodiments, a self-assembled monolayer, a polymer layer and/or other anchoring layer may be provided on the vertex, and the at least one nanoparticle may be provided on the anchoring layer, opposite the vertex. In other embodiments, the anchoring layer also may be provided on the first electrode end and on the second electrode end. In still other embodiments, an insulating layer may be provided on the vertex.

Some embodiments of the invention may be used to form an electrically-gated single-electron transistor, wherein a gate electrode is provided on the at least one nanoparticle opposite the vertex. In other embodiments, a chemically-gated single-electron transistor may be provided by providing an analyte-specific binding agent on the surface of the at least one nanoparticle.

Single-electron transistors may be fabricated, according to method embodiments of the present invention, by forming a projecting feature on a substrate that projects from a face thereof, forming a first electrode on the substrate face that extends onto the projecting feature, forming a second electrode on the substrate face that extends onto the projecting feature and that is spaced apart from the first electrode, and placing at least one nanoparticle on the projecting feature between the first and second electrodes. In some embodiments, the projecting feature is a pyramid including a vertex. A first electrode is formed on a first side of the pyramid, including a first electrode end that extends adjacent the vertex. A second electrode is formed on a second side of the pyramid including a second electrode end that extends adjacent the vertex, and that is spaced apart from the first electrode. At least one nanoparticle is placed on the vertex.

In any of the method embodiments, the projecting feature and/or pyramid may project outwardly away from the face of the substrate and/or inwardly to form a trench in the face of the substrate. In some method embodiments, the first and second electrodes may be provided by directionally depositing a conductive layer. For example, a first directional deposition may form a conductive layer on the first side of the pyramid, and a second directional deposition may form a conductive layer on the second side of the pyramid. Moreover, a plurality of spaced apart projecting features such as pyramids, a plurality of first electrodes and a plurality of second electrodes may be fabricated on a substrate. Self-assembled monolayers, insulating layers, analyte-specific binding agents and/or gate electrodes also may be fabricated. Accordingly, the geometric configuration of a feature may determine the spacing between first and second electrodes, to thereby allow a single-electron transistor to be fabricated using conventional microelectronic processing steps, while allowing high performance and/or high yields.

All features and advantages of the present invention will become apparent in the following detailed written description.

BRIEF DESCRIPTION OF THE DRAWINGS

The invention itself, as well as a preferred mode of use, further objects, and advantages thereof, will best be understood by reference to the following detailed description of an illustrative embodiment when read in conjunction with the accompanying drawings, wherein:

FIGS. 1A, 1B, 2A, 2B, 3A, 3B, 4A, 4B, 5–8, 9A and 10–11 are side cross-sectional views of single-electron transistors according to embodiments of the present invention;

DETAILED DESCRIPTION OF A PREFERRED EMBODIMENT

Figure 1A:
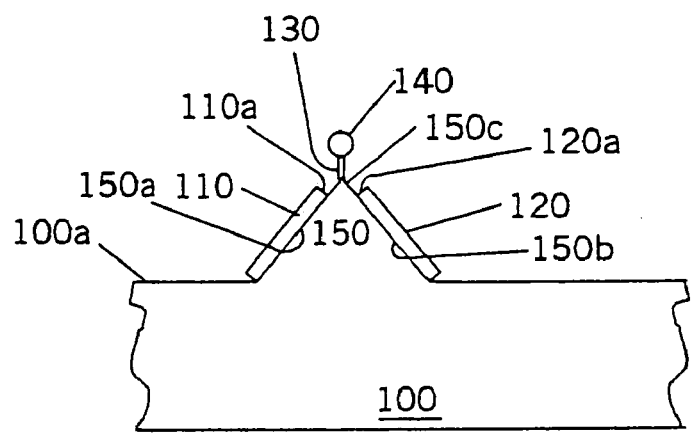

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions may be exaggerated for clarity. Like numbers refer to like elements throughout.

Figure 1B:
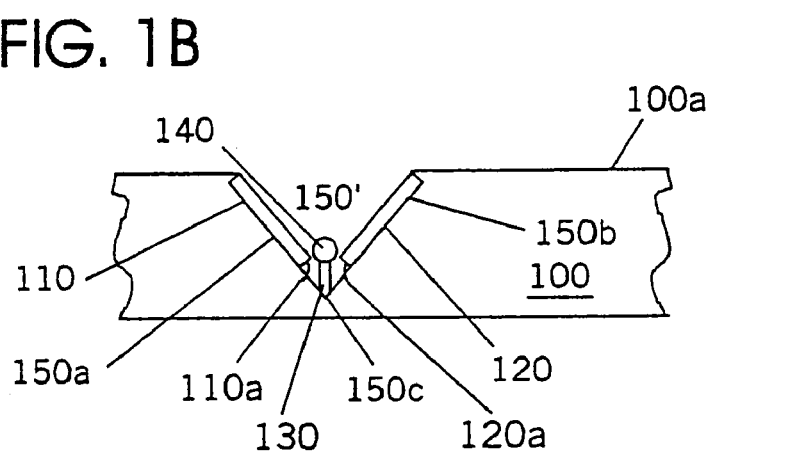
Figure 1C:
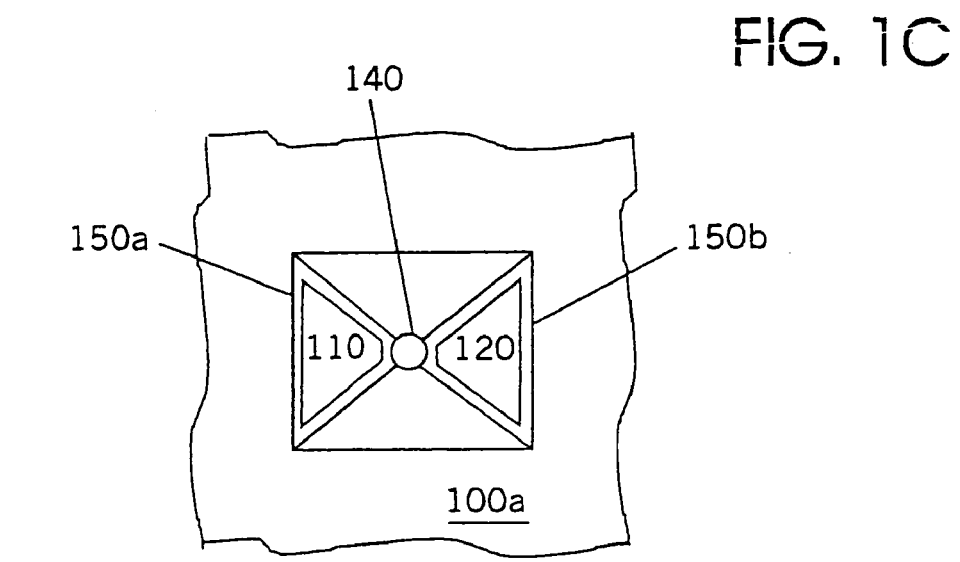
FIGS. 1C, 2C, 3C, 4C and 9B are top views of single-electron transistors according to embodiments of the present invention.

FIGS. 1A and 1B are side cross-sectional views, and FIG. 1C is a top view, respectively, of single-electron transistors according to embodiments of the present invention. As shown in FIGS. 1A and 1C, these embodiments of single-electron transistors include a substrate 100, having a face 100a. As is well known to those having skill in the art, the substrate can comprise a conventional monocrystalline silicon substrate, a semiconductor-on-insulator (SOI) substrate, a silicon carbide, gallium arsenide, gallium nitride, diamond thin film and/or other substrate, and may also include one or more heteroepitaxial and/or homoepitaxial layers on the substrate. The substrate face 100a may be planar, or non-planar (three-dimensional).

Still referring to FIGS. 1A and 1C, the substrate includes a projecting feature, such as a pyramid 150, that projects from the face 100a thereof. The projecting feature also may be regarded as a topographic feature that alters the topography of the substrate. The pyramid 150 includes a plurality of sides, including sides 150a and 150b, and an vertex 150c therebetween. It will be understood that, as used herein, the term "vertex" applies to a region on a surface of a pyramid where the sides of the pyramid intersect or approach one another. The vertex need not be the highest or lowest point of the pyramid.

In FIG. 1A, the pyramid 150 projects outwardly away from the face 100a of the substrate 100. A first electrode 110 is provided on a first side 150a of the pyramid, including a first electrode end 110a that extends adjacent the vertex 150c. A second electrode 120 is provided on a second side 150b of the pyramid 150, and including a second electrode end 120a that extends adjacent the vertex 150c, and that is spaced apart from the first electrode end 110a. The first and second electrodes 110 and 120, respectively, may be conductive, or may include a portion thereof that is conductive, at least adjacent the ends 110a and 120a thereof. The first and second electrodes may comprise any of the materials that were described above for the substrate 100, and may also include other conductive materials, such as conductive polysilicon, metal and/or other conductive materials.

Although the pyramid 150 is illustrated in FIGS. 1A and 1C as having four equally shaped and sized sides, it may have a different number of sides, and the sides need not be equal in shape or area. The sides also need not be planar. Finally, although FIGS. 1A and 1C illustrate a pyramid, other features, such as conical tips and/or polyhedral solids, which project from the substrate 100, also may be used.

Still referring to FIGS. 1A and 1C, at least one nanoparticle 140 is provided on the vertex 150c. The fabrication of at least one nanoparticle 140 is described, for example, in the above-incorporated Brousseau et al., Feldheim et al. and Klein et al. publications, and need not be described further herein.

As shown in FIG. 1A, in some embodiments, a self-assembled monolayer 130 is provided between the at least one nanoparticle 140 and the vertex 150c. Chemical interactions can be used to anchor a nanoparticle on a surface, for example, pursuant to techniques that are described in a publication to Ulman, entitled *Formation and Structure of Self-Assembled Monolayers*, Chemical Review, 1996, pp. 1533–1554. Processes which can be used to attach molecular receptor probes to surfaces using self-assembled nanolayers are described in Lenigk et al., *Surface Characterization of a Silicon-Chip-Based DNA Microarray, Langmuir*, 2001, pp. 2497–2501. The disclosures of both of these publications are hereby incorporated herein by reference in their entirety as if set forth fully herein, and need not be described further herein. Also, some polymers have shown affinity for nanoparticle adhesion, or can be chemically modified to have a strong affinity, which can be used as an anchor layer.

As shown in FIGS. 1A and 1C, the geometric configuration of the pyramid 150 may be used to control the spacing between the first electrode end 110a and the second electrode end 120a, so as to provide quantum mechanical tunneling therebetween through the at least one nanoparticle 140. Since the dimensions of the pyramid may be well-controlled on a nanometer scale using conventional microelectronic techniques, such as techniques that are used to fabricate Atomic Force Microscope (AFM) tips, the desired spacing for single-electron transistor may be obtained relatively inexpensively and/or with relatively high yields.

In embodiments of FIGS. 1A and 1C, the projecting (topographic) feature, such as the pyramid 150, projects outwardly away from the face of the substrate. In contrast, in embodiments of FIG. 1B, the projecting (topographic) feature, such as a pyramid 150' projects inwardly from the face 100a of the substrate 100, to thereby form a trench such as a pyramidal-shaped trench. The top view of FIG. 1C also applies to embodiments of FIG. 1B in which the projecting feature projects inwardly into the substrate. It will be understood that combinations of inwardly- and outwardly-projecting features such as pyramids may be used on a single substrate. The trench may have various sizes and/or shapes as was described above with respect to outwardly projecting structures.

From a dimensional standpoint, the vertex 150c may be about 0.05 μm away from the face 100a of the substrate 100, and the vertex 150c may form an angle of about 70.6°. The length of a side of the pyramid may be about 3 μm. The first and second electrodes 110 and 120 may be about 20 nm thick. However, these dimensions are merely illustrative and many other combinations of dimensions may be used. In some embodiments, the spacing between the first end 110a and the second end 120a may be less than about 20 nm. In other embodiments, the spacing may be less than about 12 nm. In yet other embodiments, the spacing is about 10 nm. Other dimensions may be used that can provide quantum-mechanical tunneling effects.

The self-assembled monolayer 130 may maintain the at least one nanoparticle 140 at a distance of about 1 nm from both the first electrode end 110a and the second electrode end 120a. However, distances of between about 0.5 nm to about 5 nm also may be used in other embodiments. Other distances also may be used.

Figure 2A:
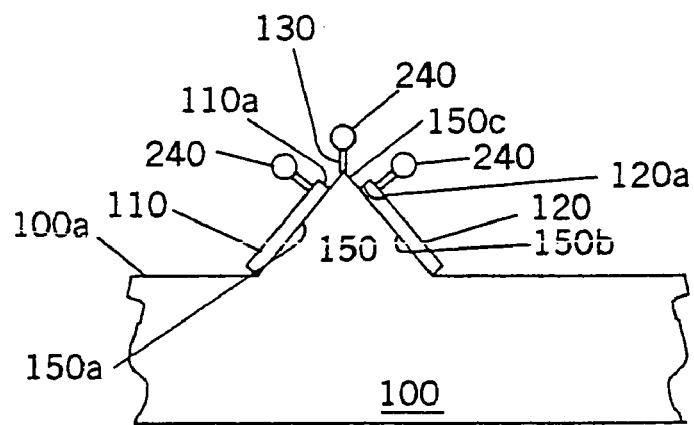
Figure 2B:
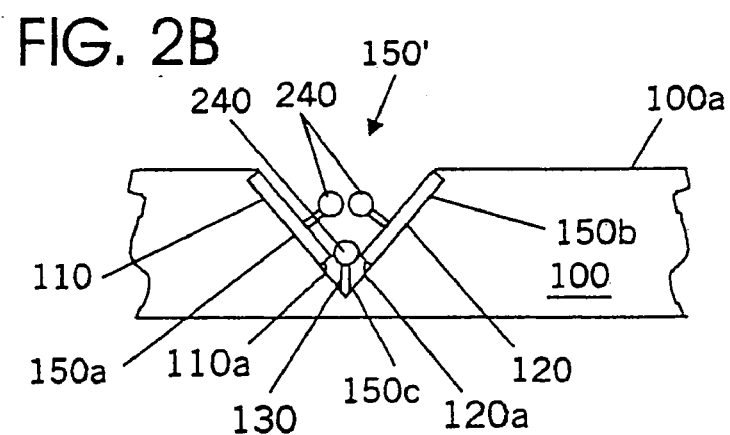
Figure 2C:
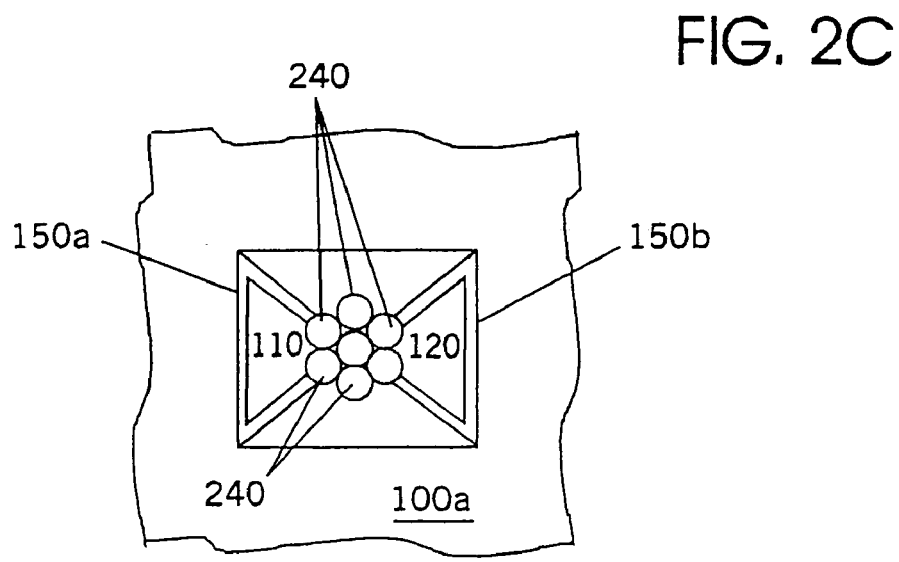

In embodiments of FIGS. 1A–1C, at least one nanoparticle 140 is provided on the vertex 150c, whereas the first electrode end 110a and the second electrode end 110b are free of nanoparticles 140 thereon. However, in other embodiments of the invention, as illustrated in FIGS. 2A–2C, a plurality of nanoparticles 240 are provided on the vertex 150c, on the first electrode end 110a and/or on the second electrode end 120a. Moreover, the plurality of nanoparticles 240 may be randomly spaced and/or may be spaced in a linear and/or nonlinear, orthogonal and/or nonorthogonal array of equally and/or unequally (aperiodic and/or random) spaced apart nanoparticles. The nanoparticles 240 may have a predetermined relationship to the underlying layers and/or a random relationship thereto.

FIGS. 3A–3C and 4A–4C are cross-sectional views of single-electron transistors according to other embodiments of the invention. In these embodiments, a flat vertex 150c' provides, for example, an Aztec-type pyramid, rather than an Egyptian-type pyramid of FIGS. 1–2. Other flat-topped projecting features also may be provided, such as a truncated cone and/or a polyhedral solid.

Figure 3A:
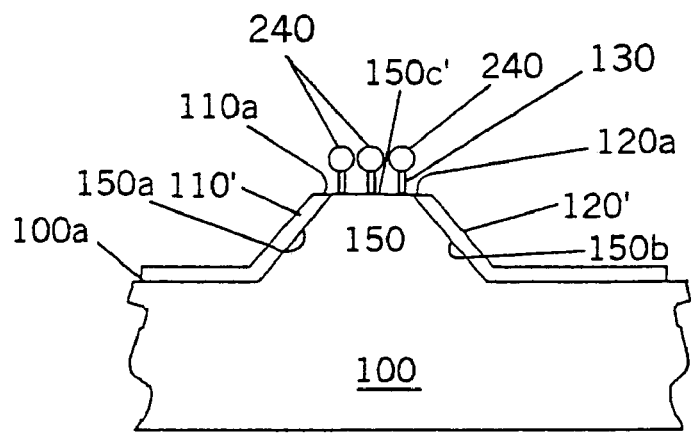
Figure 3B:
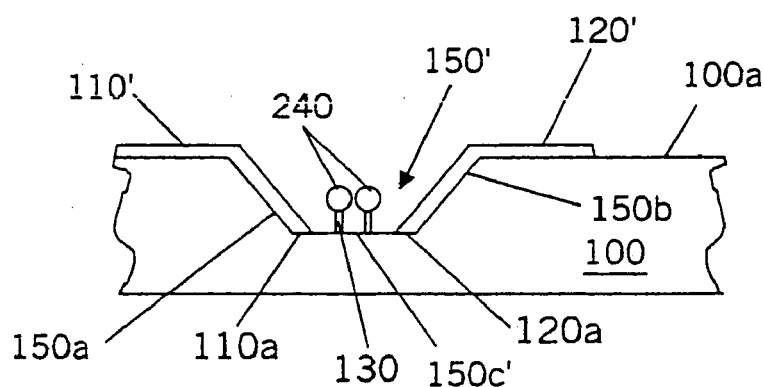
Figure 3C:
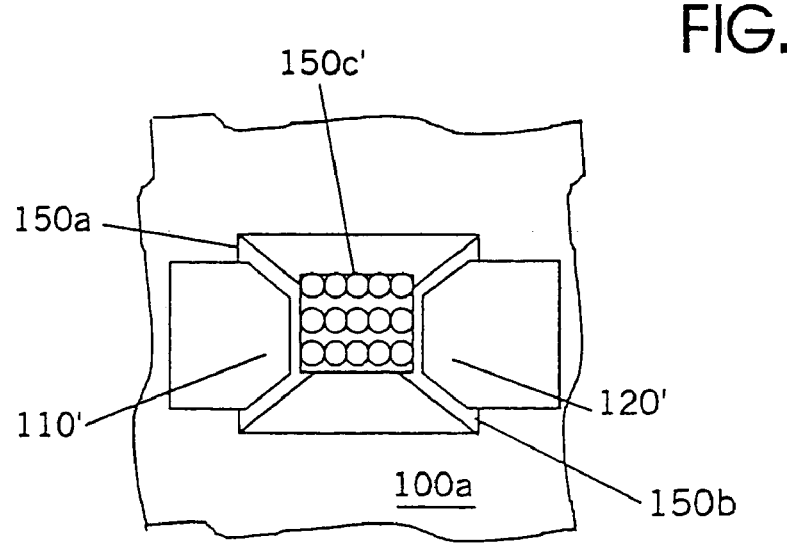

Moreover, in FIGS. 3A–3C, the first and second electrodes are extended first and second electrodes 110' and 120', that also extend along the substrate face 100a. Extended first and/or second electrodes may be provided in any of the embodiments that are described herein.

Figure 4A:
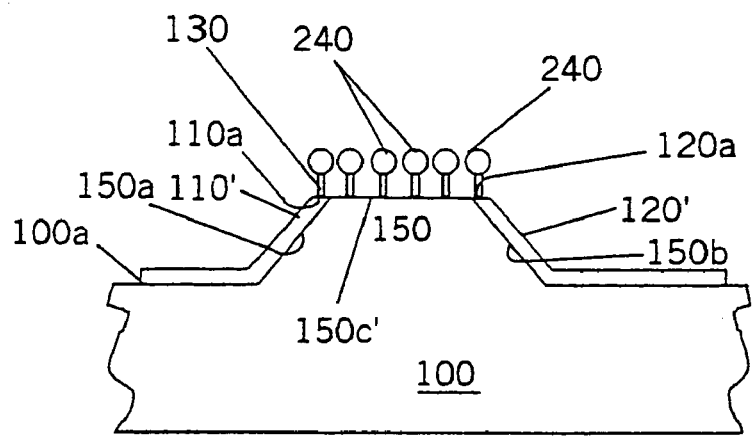
Figure 4B:
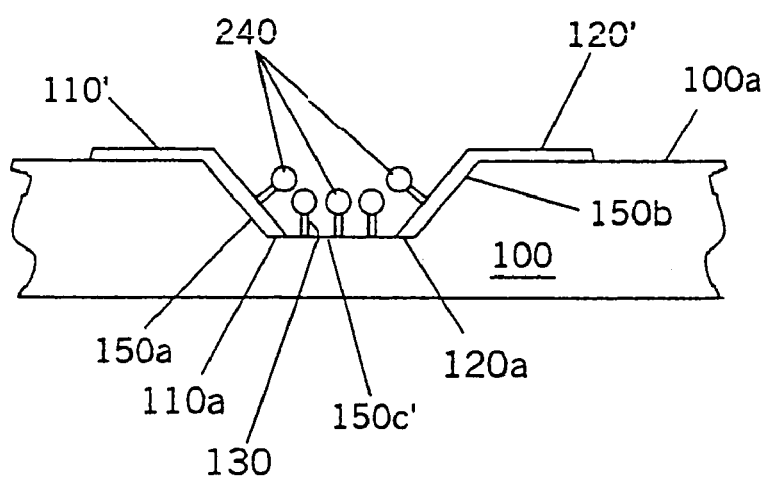
Figure 4C:
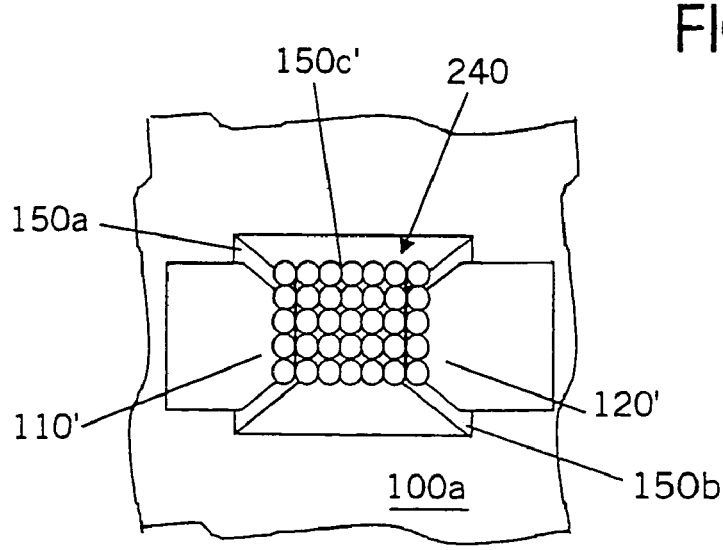

FIGS. 4A–4C describe pyramids having a flat vertex 150c', extended electrodes 110' and 120', and an array of nanoparticles 240 on the flat top 150c, on the end of the first extended electrode 110' and/or on the end of the second extended electrode 120'. Nanoparticles on the first and/or second electrode ends also may be used with any of the embodiments that are described herein.

Figure 5:
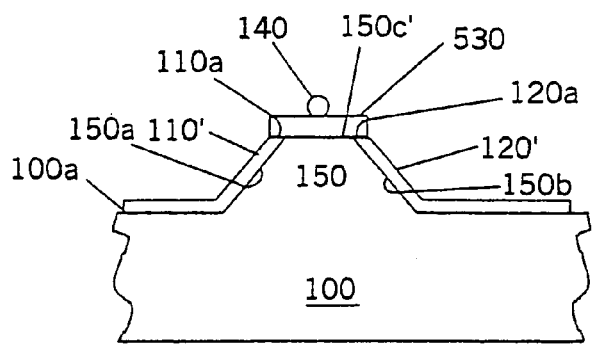
Figure 6:
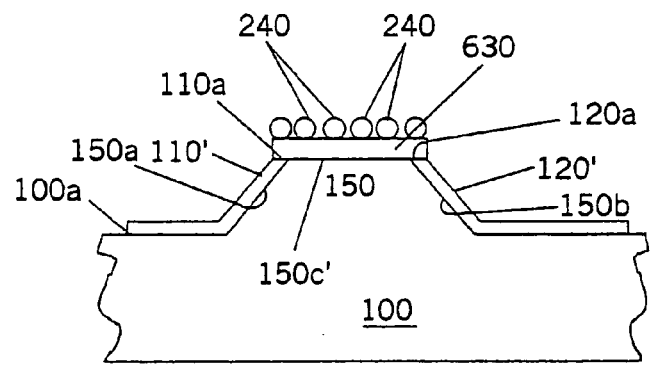

FIGS. 5 and 6 are cross-sectional views of single-electron transistors according to other embodiments of the invention. In these embodiments, an insulating layer or sublayers 530, 630 comprising silicon dioxide, silicon nitride and/or other conventional insulating materials, is provided between the at least one nanoparticle 140, 240 and the vertex 150', the first electrode end 110a and/or the second electrode end 120a. Also, some polymers have shown affinity for nanoparticle adhesion, or can be chemically modified to have a strong affinity, which can be used as an anchor layer. The use of an insulating layer to anchor a nanoparticle is described, for example, in Andres et al., *"Coulomb Staircase" Single Electron Tunneling at Room Temperature in a Self Assembled Molecular Nanostructure*, Science, 1996, Vol. 272, pp. 1323–1325, the disclosure of which is hereby incorporated herein by reference in its entirety as if set forth fully herein, and need not be described further herein. In yet other embodiments, both an insulating layer 530, 630 of FIGS. 5 and 6, and a self-assembled monolayer that is described herein, may be used in combination. Other intermediary layers also may be used.

Figure 7:
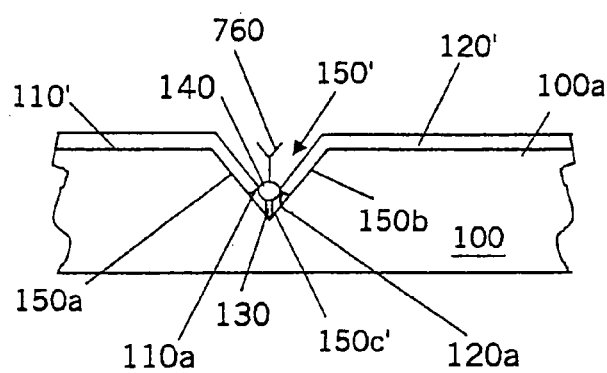

FIG. 7 is a cross-sectional view of yet other embodiments of the present invention, wherein an analyte-specific binding agent 760 is provided on a surface of the at least one nanoparticle 140, to provide a chemically-gated single-electron transistor. The analyte-specific binding agent 760 of FIG. 7 also may be provided with any of the embodiments that are described herein, to provide a chemically-gated single-electron transistor. Analyte-specific binding agents are described, for example in the above-incorporated Ulman, Lenigk et al., Feldheim et al. and Brousseau et al. publications, and need not be described further herein.

Figure 8:
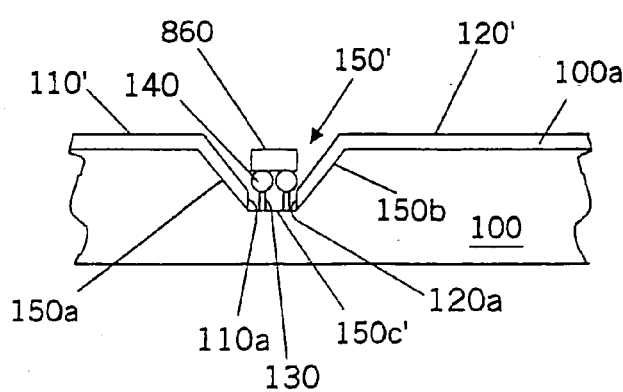

FIG. 8 is a cross-sectional view of other embodiments of the present invention, wherein a gate electrode 860 is provided on the at least one nanoparticle 140 opposite the vertex 150c, to provide a single-electron field effect transistor. Single layer and/or multilayer gate electrodes may be provided. A gate electrode also may be provided in any of the other embodiments that are described herein. An insulating layer also may be provided between the gate electrode 860 and the at least one nanoparticle, to provide an insulated gate electrode.

Figure 9A:
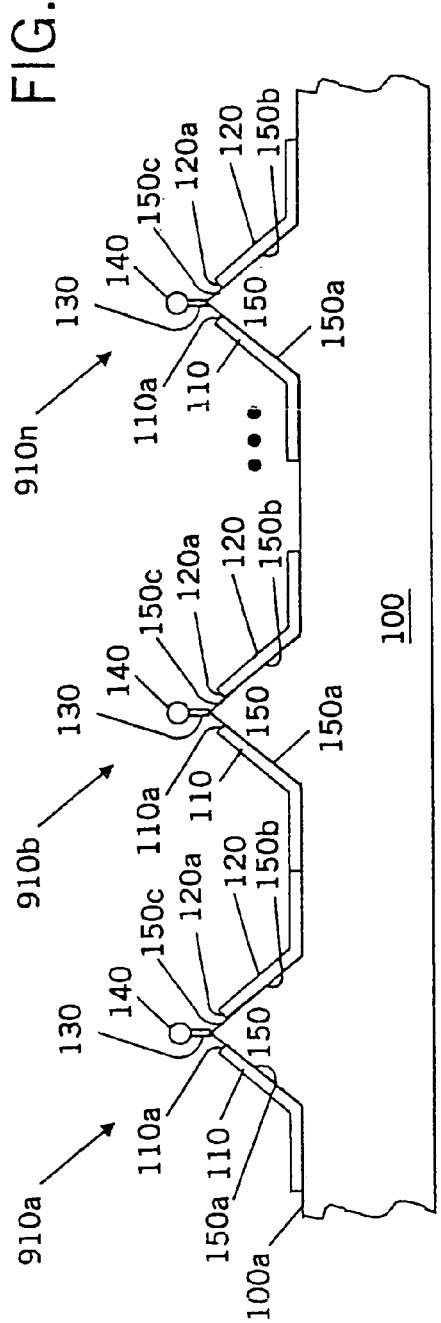
Figure 9B:
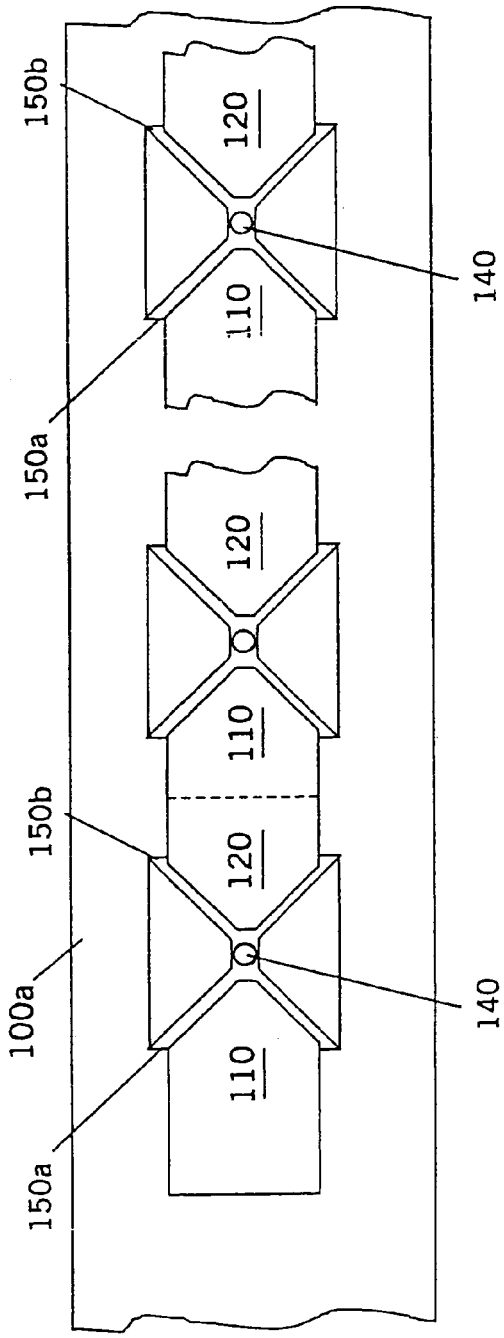

In all of the above-described embodiments, only one single-electron transistor is illustrated. However, as illustrated in FIGS. 9A–9B, an array of single-electron transistors 910a–910n may be provided on the substrate. One-and/or two-dimensional, linear and/or nonlinear, orthogonal and/or nonorthogonal arrays may be provided, with the spacing among the single-electron transistors being equal (periodic) and/or unequal (aperiodic and/or random). Each single-electron transistor 910a–910n may be identical, or at least some of the single-electron transistors may be dissimilar. Moreover, any of the embodiments described herein may be used for any of the single-electron transistors 910a–910n.

As also shown in FIGS. 9A–9B, in some embodiments, the first and second electrodes 110 and 120 between adjacent single-electron transistors can be electrically connected to one another. These configurations of the first and second electrodes also may be used with any of the embodiments of the invention that are described herein.

FIG. 10 is a cross-sectional view of an array of single-electrode transistors 1010a–1010n, wherein the first and second electrodes 1100 and 1120 are not conformal electrodes but, rather, at least partially fill the region between adjacent pyramids 150. One or more nonconformal electrodes also may be provided in any of the embodiments described herein.

As also shown in FIG. 10, in other embodiments, common backside contacts may be provided by conductive vias 1030 and conductive pads 1040. Appropriate insulating regions may be provided to electrically insulate the conductive pads 1040 from one another and/or to insulate the conductive vias 1030 from one another and/or from other regions using techniques well known to those skilled in the art. Solder bumps and/or other interconnect techniques may be used to electrically and/or mechanically connect the conductive pads 1040 to an external device. These and other external contact schemes may be used with any of the embodiments of the invention that are described herein. By providing common contacts, the number of contacts used to address individual single-electron transistors in an array of single-electron transistors may be reduced. The common contacts and/or contacting schemes of FIG. 10 may be used with any of the embodiments described herein.

Figure 11:
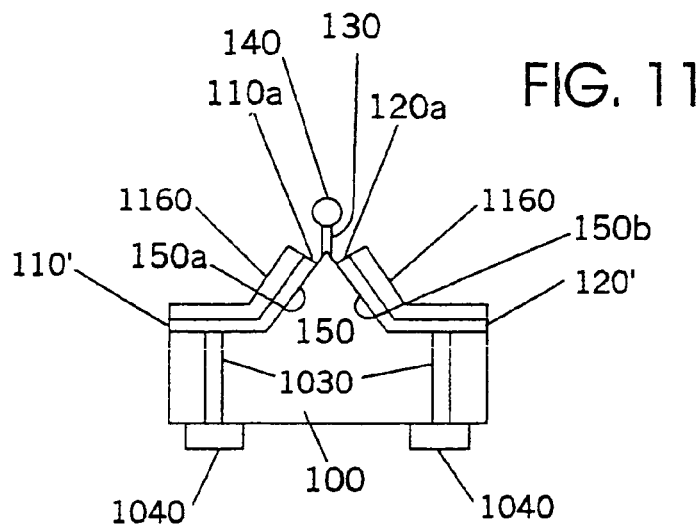

FIG. 11 is a cross-sectional view of other embodiments of the present invention. In FIG. 11, extended first and second electrodes 110' and 120' are provided along with a backside contact scheme, including conductive vias 1030 and contact pads 1040, that were described in connection with FIG. 10.

Moreover, FIG. 11 also illustrates the use of an insulating layer 1160 on the extended first and second electrodes 110' and 120', opposite the substrate 100. The insulating layer 1160 may comprise a layer or multiple sublayers comprising silicon dioxide, silicon nitride, one or more self-assembled monolayers, one or more polymer films and/or other materials that may be used to protect a device from an outside (ambient) environment. The insulating layer 1160 may be a specialized layer that may depend upon the ambient in which a chemically-gated single-electron transistor is being used. The insulating layer 1160 may be used with or without the extended first and second electrodes 110' and 120' of FIG. 11, and/or with any of the other embodiments that are described herein.

FIGS. 12A–12E are cross-sectional views of single-electron transistors according to embodiments of the present invention, during intermediate fabrication steps according to embodiments of the present invention. These method embodiments may be used to fabricate single-electron transistors as illustrated in FIG. 11. However, similar method embodiments may be used to fabricate other single-electron transistors as described herein.

Figure 12A:
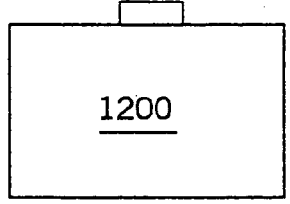
FIGS. 12A–12E, 13A–13F and 14A–14E are side cross-sectional views of single-electron transistors according to embodiments of the present invention during intermediate fabrication steps according to embodiments of the present invention.

Referring now to FIG. 12A, a mask region 1210 is formed on a substrate 1200, for example by forming a conventional mask comprising silicon nitride on a conventional substrate, and then patterning using conventional photolithography. It will be understood that since the width of the mask region 1210 need not determine the spacing between the first and second electrodes that are formed subsequently, conventional photolithography may be used. It also will be understood that the substrate 1200 may be a conventional substrate, as was described in connection with FIG. 1A, such as a layer of doped polysilicon and/or other conductive material on a monocrystalline silicon substrate.

Figure 12B:
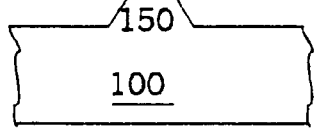

Then, referring to FIG. 12B, an anisotropic (wet) etch, an isotropic etch such as a Reactive Ion Etch (RIE) and/or other conventional etching process may be performed using the masking region 1210 as an etch mask, to form the feature such as the pyramid 150 on a substrate 100. Other conventional etching techniques and/or other conventional tip-forming techniques such as selective epitaxial growth, may be used.

Figure 12C:
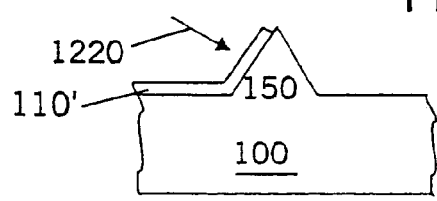

Referring now to FIG. 12C, the mask region 1210 is removed. The first electrode 110' is formed, for example, by performing a directional (angled) evaporation and/or other directional deposition in a direction shown by arrow 1220. The directional evaporation in the direction 1220 can form a first electrode 110' on the first side 150a of the pyramid 150. It will be understood that portions of the substrate may be masked as appropriate, to provide conductive connections on the substrate face.

Figure 12D:
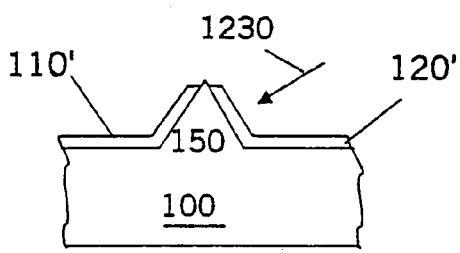

Then, referring to FIG. 12D, a second directional (angled) deposition and/or evaporation in a direction 1230 is performed to form the second electrode 120' on the second side 150b of the pyramid 150. It will be understood that portions of the substrate may be masked as appropriate, to provide conductive connections on the substrate face. It also will be understood that during and/or after the angled evaporations of FIGS. 12C and 12D, sufficient heat may be applied so that, upon cooling, surface tension pulls back the first and second ends 110a and 120a of the first and second electrodes 110' and 120' sufficiently away from the vertex 150c, so as not to join at the vertex 150a. Accordingly, two closely spaced apart electrodes are formed.

Figure 12E:
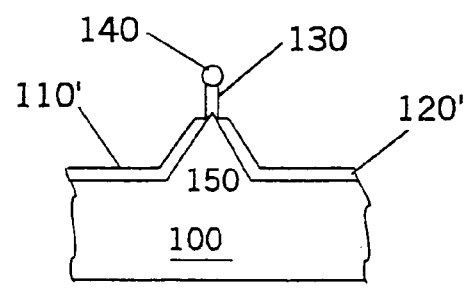

Finally, referring to FIG. 12E, absorption of the anchoring self-assembled monolayer 130 may be performed, for example using techniques that were described above. At least one nanoparticle 140 is then attached to the anchoring self-assembled monolayer 130, a polymer layer and/or other anchoring layer, for example using techniques that were described above. Vias and/or pads may be formed, before, during and/or after any of the steps that were described in FIGS. 12A–12E FIGS. 13A–13F are cross-sectional views of other single-electron transistors according to embodiments of the present invention, during intermediate fabrication steps according to embodiments of the present invention. These method embodiments may be used to fabricate single-electron transistors as illustrated in FIG. 11. However, similar method embodiments may be used to fabricate other single-electron transistors as described herein.

As shown in FIGS. 12A–12D, first and second electrodes are formed on a pyramid or other projecting feature similar to FIGS. 12A–12D. Then, referring to FIG. 13E, a recessed layer 1310 is formed between the pyramids 150. The recessed layer 1310 may include one or more sublayers comprising silicon dioxide, silicon nitride, polyimide and/or other materials that are compatible with a subsequent selective etching and/or chemical-mechanical polishing process. The recessed layer 1310 may be recessed from the vertex by a distance that is determined by the desired spacing between the first and second electrodes 110' and 120'.

Figure 13A:
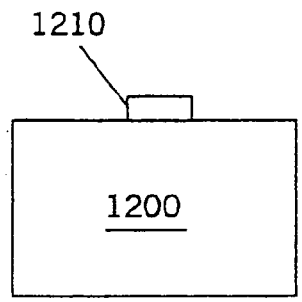
Figure 13B:
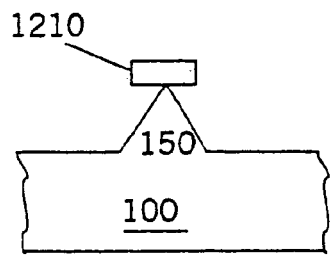
Figure 13C:
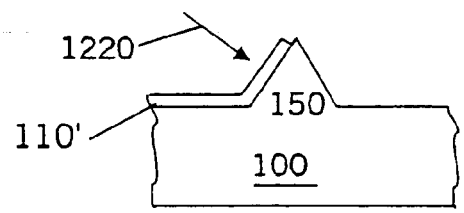
Figure 13D:
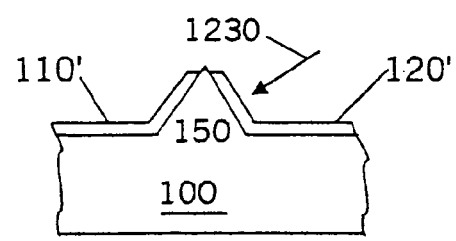
Figure 13E:
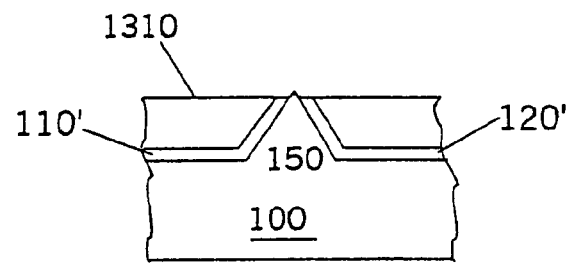
Figure 13F:
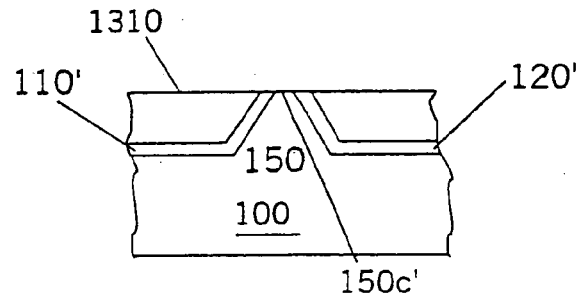

Referring now to FIG. 13F, chemical-mechanical polishing and/or other conventional techniques are used to planarize the structure, and thereby define the flat vertex 150c'. The recessed layer 1310 then may be removed and at least one nanoparticle 140 and an optional self-assembled monolayer 130, polymer layer and/or other anchoring layer are formed, as was described in connection with FIG. 12E. Vias and/or pads also may be fabricated, as was described above.

Finally, FIGS. 14A–14E are cross-sectional views of single-electron transistors according to other embodiments of the present invention during intermediate fabrication steps according to other method embodiments of the present invention. These method embodiments may be used to fabricate single-electron transistors as illustrated in FIG. 7. However, similar method embodiments may be used to fabricate other single-electron transistors as described herein.

Figure 14A:
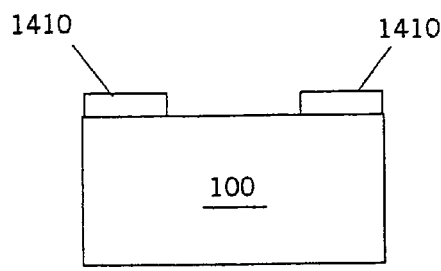
Figure 14B:
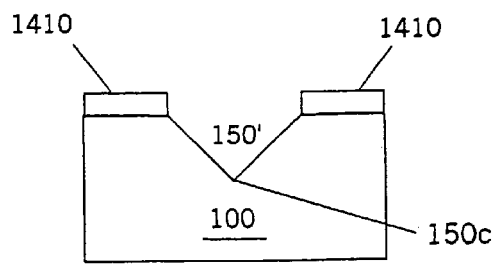

Referring now to FIG. 14A, a mask region 1410 is formed on a substrate 1400, for example as was described in connection with FIG. 10A. Then, referring to FIG. 14B, an etch such as an anisotropic and/or isotropic etch may be performed using the mask region 1410 as an etching mask, to form the pyramid-shaped trench 150' in the substrate 100. Other conventional etching techniques and/or other recessed feature forming techniques also may be used.

Figure 14C:
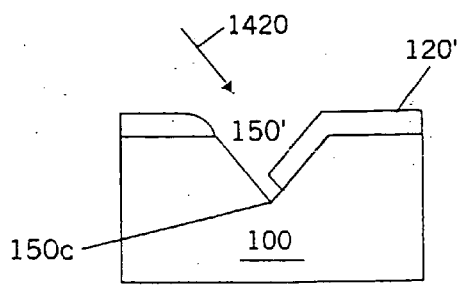
Figure 14D:
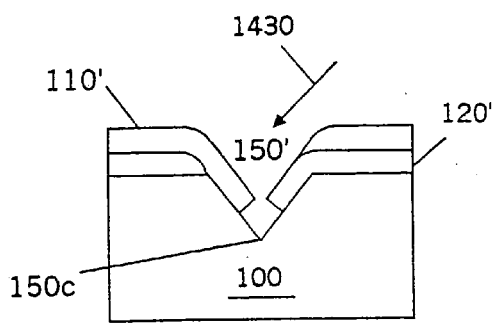

Referring now to FIG. 14C, the mask region 1410 may be removed, and the second electrode 120' is formed, for example by performing directional (angled) deposition in the direction 1420, similar to that which was described in connection with FIG. 12C. Then, referring to FIG. 14D, a second directional deposition may be performed, for example along direction 1430, in a manner similar to that which was described in connection with FIG. 12D, to thereby form the first electrode 110'.

Figure 14E:
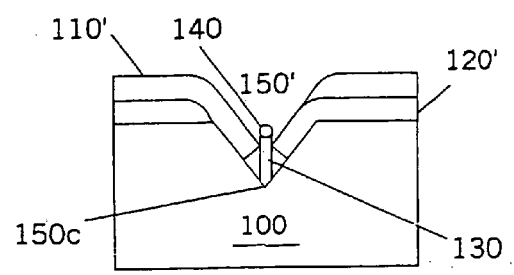

Finally, referring to FIG. 14E, absorption of the anchoring self-assembled monolayer 130, polymer layer and/or other anchoring layer may be performed, for example, using techniques that were described above. At least one nanoparticle 140 that is attached to the anchoring self-assembled monolayer 130, for example, using techniques that were described above. Vias and/or pads also may be fabricated, as was described above.

Accordingly, embodiments of the present invention can provide arrays, including large arrays, of closely spaced apart electrodes. These electrodes can allow electrochemical reactions to be monitored at the vertexes of each pyramid and/or other protruding feature. The electrodes may be derivatized to include chemical specificity to reactions taking place at the surfaces. Enhanced sensitivity can be made possible by attaching nanometer-sized colloidal particles to the regions between the electrodes, which can create single-electron transistors. The colloids can be functionalized with chemically-specific receptors and/or molecules, to incorporate specificity to these reactions. For example, a polynucleic acid, such as cDNA, oligonucleotides, aptamer, or mRNA can be used as the analyte-specific binding agent for detecting the complementary target in solution. As another example, an enzyme, antibody or protein can be used as the analyte-specific binding agent for detecting a corresponding antigen, ligand, or substrate in a sample. As yet another example, small molecules such as drugs, ligands, antigens, substrates or hapten can be used as the analyte-specific binding agent for detecting other molecules in solution. Those skilled in the art will recognize that other biological and chemical species are useful as analyte-specific binding agents and/or targets, and that other combinations are possible than those listed above.

Single-electron transistors or arrays thereof, according to embodiments of the invention, may be used, for example, as sensing platforms in the wells of microtiter plates, for biological assays. Their enhanced sensitivity compared to conventional larger electrodes can benefit drug discovery and/or biochemistry. Their small size also can afford direct insertion of the arrays into living cells, which can allow in vivo chemical study and/or direct mapping of chemical pathways and/or concentrations within the cells.

While the invention has been particularly shown and described with reference to a preferred embodiment, it will be understood by those skilled in the art that various changes in form and detail may be made therein without departing from the spirit and scope of the present invention.

What is claimed is:

1. A single-electron transistor comprising:
   a substrate having a projection that projects from a face thereof, wherein said projection includes a plurality of sides and a vertex;
   a first electrode on a first side of said projection and including a first electrode end that extends adjacent said vertex;
   a second electrode on a second side of said projection and including a second electrode end that extends adjacent said vertex and that is spaced apart from said first electrode end;
   at least one nanoparticle on said vertex, and
   an analyte-specific binding agent on a surface of said at least one nanoparticle to provide a chemically gated single-electron transistor, wherein said analyte-specific binding agent is a polynucleic acid selected from the group consisting of DNA, oligonucleotides, aptamer and RNA.

2. A single-electron transistor comprising:
   a substrate having a projection that projects from a face thereof, wherein said projection includes a plurality of sides and a vertex;

a first electrode on a first side of said projection and including a first electrode end that extends adjacent said vertex;

a second electrode on a second side of said projection and including a second electrode end that extends adjacent said vertex and that is spaced apart from said first electrode end;

at least one nanoparticle on said vertex; and an analyte-specific binding agent on a surface of said at least one nanoparticle to provide a chemically gated single-electron transistor, wherein said analyte-specific binding agent is a polyaminoacid selected from the group consisting of enzyme, antibody and protein.

3. A single-electron transistor comprising:

a substrate having a projection that projects from a face thereof, wherein said projection includes a plurality of sides and a vertex;

a first electrode on a first side of said projection and including a first electrode end that extends adjacent said vertex;

a second electrode on a second side of said projection and including a second electrode end that extends adjacent said vertex and that is spaced apart from said first electrode end;

at least one nanoparticle on said vertex; and an analyte-specific binding agent on a surface of said at least one nanoparticle to provide a chemically gated single-electron transistor, wherein said analyte-specific binding agent are small molecules selected from the group consisting of drugs, ligands, antigens, substrates and hapten.

4. The single-electron transistor of claim 1, wherein said projection is a pyramid.

5. The single-electron transistor of claim 2, wherein said projection is a pyramid.

6. The single-electron transistor of claim 3, wherein said projection is a pyramid.

* * * * *